United States Patent
Muramatsu et al.

(10) Patent No.: US 6,572,851 B2
(45) Date of Patent: *Jun. 3, 2003

(54) METHOD FOR SUPPRESSING OR TREATING DRUG-INDUCED NEPHROPATHY

(75) Inventors: Takashi Muramatsu, Aichi (JP); Kenji Kadomatsu, Aichi (JP); Munehiro Oda, Kanagawa (JP); Shinya Ikematsu, Kanagawa (JP); Sadatoshi Sakuma, Kanagawa (JP)

(73) Assignee: Takashi Muramatsu (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/380,882
(22) PCT Filed: Mar. 12, 1998
(86) PCT No.: PCT/JP98/01050
§ 371 (c)(1),
(2), (4) Date: Dec. 2, 1999
(87) PCT Pub. No.: WO98/40095
PCT Pub. Date: Sep. 17, 1998

(65) Prior Publication Data
US 2002/0019333 A1 Feb. 14, 2002

(30) Foreign Application Priority Data
Mar. 12, 1997 (JP) ............................................. 9-074684

(51) Int. Cl.$^7$ .................... A61K 38/00; A61K 45/00; C07K 14/00
(52) U.S. Cl. .................... 424/85.1; 424/198.1; 514/2; 514/12; 530/350; 530/399
(58) Field of Search .................. 514/2, 8, 12; 424/85.1, 424/198.1; 530/350, 300, 399; 435/4

(56) References Cited

U.S. PATENT DOCUMENTS

| 5,210,026 A | 5/1993 | Kovesdi et al. ............ 435/69.1 |
| 5,288,487 A | 2/1994 | Kawashima et al. ....... 424/85.1 |
| 5,466,678 A | 11/1995 | Kawabata et al. ............ 514/46 |

FOREIGN PATENT DOCUMENTS

| EP | 0385385 | 9/1990 |
| EP | 0535336 | 4/1993 |
| EP | 0535337 | 4/1993 |
| EP | 0620004 | 10/1994 |
| WO | 9405299 | 3/1994 |
| WO | 962257 | 2/1996 |

OTHER PUBLICATIONS

Gilman, ed. 1993. Goodman and Gilman's The Pharmacological Basis of Therapeutics. New York: McGraw–Hill, Inc.; p. 1202–1263.*

Elseviers et al. Analgesic Nephropathy: Is it caused by multi–analgesic or single substance abuse? Drug Safety 20(1): 15–24, 1999.*

Gilman, ed. 1993. Goodman and Gilman's The Pharmaceutical Basis of Therapeutics. New York: McGraw–Hill, Inc.; p. 1249–1252.*

Kurtz, Andreas et al. (1995) "Pleiotrophin and Midkine in Normal Development and Tumor Biology" *Critical Reviews in Oncogenesis* 6(2):151–177.

Kadomatsu, Kenji et al. (1988) "cDNA Cloning and Sequencing of a New Gene Intensely Expressed in Early Differentiation Stages of Embryonal Carcinoma Cells and in Mid–Gestation Period of Mouse Embryogenesis" *Biochemical and Biophysical Research Communications* 151(3):1312–1318.

Rauvala, Heikki (1989) "An 18–kd heparin–binding protein of developing brain that is distinct from fibroblast growth factors" *The EMBO Journal* 8(10):2933–2941.

Muramatsu, Takashi (1993) "Midkine (MK), the product of a retinoic acid responsive gene, and pleiotrophin constitute a new protein family regulating growth and differentiation" *Int. J. Dev. Biol.* 37:183–188.

Muramatsu, Takahashi (1994) "The Midkine Family of Growth/Differentiation Factors" *Develop. Growth & Differ.* 36(1):1–8.

Ratovitski, Edward A. et al. (1998) "Midkine Induces Tumor Cell Proliferation and Binds to a High Affinity Signaling Receptor Associated with JAK Tyrosine Kinases" *The Journal of Biological Chemistry* 273(6):3654–3660.

Studier, F. William et al. (1990) "Use of T7 RNA Polymerase to Direct Expression of Cloned Genes" *Methods Enzymol.* 185:60–89.

Tsutsumi, Yasuo et al. (1997) "PEGylation of Interleukin–6 Effectively Increases Its Thrombopoietic Potency" *Thrombosis and Haemostasis* 77(1):168–173.

* cited by examiner

Primary Examiner—Elizabeth Kemmerer
Assistant Examiner—Bridget E. Bunner
(74) Attorney, Agent, or Firm—Saliwanchik, Lloyd & Saliwanchik

(57) ABSTRACT

The present invention provides a novel drug for relieving drug-induced nephropathy and acute hepatopahy containing a midkine (MK) family protein such as pleiotrophin (PTN). The MK family proteins can inhibit nephropathy induced by an antitumor agent or acute hepatopathy caused by carbon tetrachloride and thus effectively relieve drug-induced nephropathy or hepatopathy.

4 Claims, 12 Drawing Sheets

MQAQQYQQQRRKFAAAFLAFIFILAAVDTAEAGKKEKPEKKVKKSDCGEWQWSVCVPTSG
DCGLGTREGTRTGAECKQTMKTQRCKIPCNWKKQFGAECKYQFQAWGECDLNTALKTRTG
SLKRALHNAECQKTVTISKPCGKLTKPKPQAESKKKKKEGKKQEKMLD

FIGURE 11A

MSSQQYQQQRRKFAAAFLALIFILAAVDTAEAGKKEKPEKKVKKSDCGEWQWSVCVPTSG
DCGLGTREGTRTGAECKQTMKTQRCKIPCNWKKQFGAECKYQFQAWGECDLNTALKTRTG
SLKRALHNAECQKTVTISKPCGKLTKPKPQAESKKKKKEGKKQEKMLD

FIGURE 11B

MSSQQYQQQRRKFAAAFLALIFILAAVDTAEAGKKEKPEKKVKKSDCGEWQWSVCVPTSG
DCGLGTREGTRTGAECKQTMKTQRCKIPCNWKKQFGAECKYQFQAWGECDLNTALKTRTG
SLKRALHNAECQKTVTISKPCGKLTKPKPQAESKKKKKEGKKQEKMLD

FIGURE 11C

MQTPQYLQQRRKFAAAFLAFIFILAAVDTAEAGKKEKPEKKVKKSDCGEWQWSVCVPTSGD
CGLGTREGTRTGAECKQTMKTQRCKIPCNWKKQFGAECKYQFQAWGECDLNTALKTRTGS
LKRALHNAECQKTVTISKPCGKLTKSKPQAESKKKKKEGKKQEKMLD

FIGURE 11D

GKKEKPEKKAKKSDCGEWQWSVCVPTNGDCGLGTREGTRTGAECKQTTKTQKCKIPCNW
KKQFGAECKYQFQAWGECDLNTALKTRTGNLKRALHNAECQKTVTISKPCGKLTKPKPQZE
KKKKKEGKKQEKMLB

FIGURE 11E

MQHRGFLLLTLLALLALTSAVAKKKDKVKKGGPGSECAEWAWGPCTPSSKDCGVGFREGT
CGAQTQRIRCRVPCNWKKEFGADCKYKFENWGACDGGTGTKVRQGTLKKARYNAQCQETI
RVTKPCTPKTKAKAKAKKGKGKD

FIGURE 12A

MQHRGFFLLALLALLVVTSAVAKKKEKVKKGSECSEWTWGPCTPSSKDCGMGFREGTCGA
QTQRVHCKVPCNWKKEFGADCKYKFESWGACDGSTGTKARQGTLKKARYNAQCQETIRV
TKPCTSKTKSKTKAKKGKGKD

FIGURE 12B

MQPRGLLLLLALLLLAAAAEAAKAKKEKMKKEGSECQDWHWGPCIPNSKDCGLGYREGSC
GDESRKLKCKIPCNWKKKFGADCKYKFESWGGCSAKTGVKTRSGILKKALYNAECEEVVY
VSKPCTAKMKAKAKAKKGKGKD

FIGURE 12C

MELRAFCVILLITVLAVSSQAAKNKKEKGKKGASDCTEWTWGSCIFNSKDCGAGTREGTCK
EETRKLKCKILCNTKKAFGADCKYKFENTGECNATTGNKVRSGTLKKALYNADCQQTVEAT
KPCSLKTKSKSKGKKGKGKE

FIGURE 12D

METHOD FOR SUPPRESSING OR TREATING DRUG-INDUCED NEPHROPATHY

TECHNICAL FIELD

The present invention relates to drugs for relieving drug-induced nephropathy and hepatitis.

BACKGROUND ART

The use of drugs for therapeutic and/or diagnostic purposes has increased year by year, and the drugs used have diversified. These drugs can provide us significant benefits but can also cause substantially harmful effects, especially to kidneys, due to their specific functions described below.

Kidneys weigh less than one percent of the total body weight. From a physiological viewpoint, 25 percent of the total cardiac output flows into the kidneys; 150 liters of primitive urine, up to 50 times the total blood plasma, is filtered through glomeruli per day; and final urine is made by reabsorption, secretion, and metabolism through uriniferous tubules variable in structural and functional heterogeneity. Thus, drugs or their metabolites in blood always circulate, and these substances are concentrated and metabolized in kidneys. Consequently, various highly concentrated metabolites, including original drugs, are distributed in kidneys. Kidneys are likely to be frequently and intensively exposed to drugs. Four types of drugs may induce nephropathy: antimicrobial agents, nonsteroidal agents, contrast agents, and antitumor agents.

The liver can also be easily damaged by drugs. Drug-induced hepatopathy is classified by its onset mechanism into toxic hepatopathy caused by direct attack of drugs or their intermediate metabolites to the liver, and allergic hepatopathy caused by allergic response, type IV delayed allergic response in which T cells are involved. Drug-induced hepatitis is caused by, most frequently, antibiotics, followed by drugs for the central nervous system, drugs for circulatory organs, antitumor agents, hormonal agents, diagnostic agents, etc.

Attempts have been made to relieve drug-induced disorders by using γ-globulin, cytochrome C, adenine, SH compounds, vitamin B group, etc., but they are not sufficiently effective. It is very important to clinically cure drug-induced disorders (side effects) because of the interruption of the treatment and the importance of patients' quality of life (Q.O.L.).

DISCLOSURE OF THE INVENTION

An objective of the present invention is to drugs that effectively relieve or suppress disorders induced by various drugs, especially by antitumor agents.

The inventors have focused on the facts that proteins belonging to the midkine (MK) family such as midkine (MK) and pleiotrophin (PTN) are growth and differentiation factors with multiple functions. The functions include 1) elongation of neurite, 2) activation of fibrinolytic system, 3) strong expression in human cancerous areas, and 4) cure of wounds. Numerous studies have been performed on such proteins in order to find novel pharmaceutical effects.

Midkine was discovered as a product of the gene whose expression was induced in the early stage of the differentiation process with retinoic acid in mouse embryonic tumor cells (Kadomatsu, K. et al., Biochem. Biophys. Res. Commun., 151: 1312–1318, 1988). Pleiotrophin was discovered in the brain of a newborn rat as a heparin-binding protein with neurite elongation ability (Rauvala, H., EMBO J., 8: 2933–2941, 1989). Midkine and Pleiotrophin form a novel class of growth and differentiation factors as heparin-binding proteins. They exhibit 45% homology and are collectively called the MK family (Muramatsu, T., Int. J. Dev. Biol., 37: 183–188, 1993; Muramatsu, T., Develop. Growth & Differ. 36(1): 1–8, 1994). Midkine and Pleiotrophin each exhibits a specific expression pattern in development processes, and is expected to be involved in important physiological activation in differentiation.

The inventors found that MK inhibits cell death caused by antitumor agents in vitro and that MK gene relieves disorders induced by an antitumor agent from the results of an experiment in which an antitumor agent was administered to knockout mice in which MK gene was functionally destroyed. The inventors also found that administering MK or PTN to wild mice relieves the disorders caused by antitumor agents, to complete the invention. The present invention encompasses each invention described in the claims.

In this invention, knockout mice provided an opportunity to investigate how MK gene in the living body fights against disorders caused by drugs and to analyze how each knockout mouse responds to the forced administration of MK at the individual level. Details of MK's function and mechanism are presently not clear. If MK functions as a trigger protein for the functional cascade of cytokines or growth factors, a very small amount of MK is presumably needed, and the use of knockout mice becomes more important. Recently, a cell surface receptor specifically binding to MK with high affinity (molecular weight 250+kDa) has been discovered. Its characteristics imply that autocrine stimulated by MK in tumor cell proliferation could be mediated by the receptor and would activate the JAK/STAT pathway (Edward, A. R. et al., J. Biol. Chem. 273: 3654–3660, 1998).

To clarify the relationship between MK and ontogenesis, homozygous MK gene-knocked out mice in which parts of exon 2 and exon 3 are damaged as illustrated in FIG. 1 were prepared (Biochemistry 7, Heisei 8: Volume 68, pp. 1239, 4-P-1244). Those knockout mice did not die during the fetal period and weighed significantly less than heterozygous or wild types (Biochemistry 7, Volume 68, pp. 1239, 4-P-1244, 1996).

Antitumor agents were administered to the knockout mice (simply referred as knockout mice) and wild mice. Survival rate, blood urea nitrogen (BUN) level, and creatinine level of each mouse were compared as indices of disorders after the administration to monitor the ability of MK gene in the living body to relieve disorders caused by antitumor agents. BUN and creatinine levels can be used as indices of functional disorders in kidneys because urea is accumulated in blood due to the reduced renal excretory ability.

In this invention, cisplatin was administered to the knockout mice and wild mice, then BUN level and survival rate were compared. The BUN level of the knockout mice were significantly higher than that of the wild mice. The survival rate of the knockout mice also differed significantly from that of wild mice. The death rate of knockout mice increased by the seventh day after the administration. The rate of abnormal BUN levels in knockout mice that had been forcedly administered MK was significantly lower than that in the group that had been administered physiological saline by the third day after the administration. The effectiveness of MK in suppressing renal cell disorders caused by cisplatin was confirmed by conducting an experiment in vitro using human infantile renal cancer cell lines. An experiment using the wild mice revealed that MK relieved acute hepatopathy due to carbon tetrachloride, and that both PTN and MK effectively suppress nephropathy caused by cisplatin.

These results indicate that proteins of this invention belonging to the MK family effectively relieve or suppress drug-induced nephropathy and hepatopathy.

MK protein (simply referred to as MK) used as an effective ingredient of the pharmaceutical composition of the invention is described in the following references (human MK gene, unexamined published Japanese patent application (JP-A) No. Hei 5-91880; sequences of the human MK gene and protein, JP-A No. Hei 6-217778; MK protein, JP-A No. Hei 5-229957; Muramatsu, T., Develop. Growth & Differ. 36(1), 1–8, 1994). PTN protein used as an effective ingredient of the pharmaceutical composition of the invention is described in the following references (Muramatsu, T., Develop. Growth & Differ. 36(1), 1–8, 1994; Kurtz, A. et al., Critical Reviews in Oncogenesis, 6(2):151–177, 1995). FIGS. 11 and 12 show the amino acid sequence of PTN and MK proteins, respectively. The proteins belonging to the MK family and used as effective ingredients of the pharmaceutical composition of this invention include natural proteins derived from humans, mice, or other mammals, or artificial proteins manufactured by chemical synthesis or genetic engineering. Also, the proteins of the invention that belong to the MK family include proteins or polypeptides which do not cause any changes of the above-described biological activities and differ from proteins derived from nature in the number or the sequences of amino acids. Specifically, the present invention includes proteins corresponding to natural proteins in which the amino acid sequence of natural proteins is partially deleted or replaced by other amino acids, or other amino acids or polypeptide of different length are inserted or added. Amino acids to be replaced or inserted are not limited to natural types.

The expression system using *E. coli* (Studier, F. W. & Moffatt, B. A., J. Mol. Biol. 189: 113–130, 1989; Studier, F. W. et al., Meth. Enzymol. 185: 60–89, 1990) or the expression system using baculovirus (O'Reilly, D. R. et al., Baculovirus Expression Vectors, A Laboratory Manual, Oxford University Press, 1992, Ausubel, F. M. et al. eds., Current Protocol in Molecular Biology, Unit 16.11, Wiley Interscience, 1994) can be used to obtain the MK family proteins that are effective ingredients of the invention using genetic engineering techniques. The inventors employed the expression system using methyl alcohol dependent yeast *Pichia pastoris* to obtain the MK proteins (refer to JP-A No. Hei 9-95454).

The pharmaceutical composition of the invention contains the MK family protein in an amount effective to prevent or treat nephropathy or hepatopathy caused by drugs. The effective ingredients of the invention can be prepared in a desirable dosage form by mixing with usually used pharmaceutically acceptable carriers, vehicles, diluents, preservatives, stabilizers, buffers, etc.

The pharmaceutical composition of the invention can be administered orally or parenterally. Dosage forms for oral administration include tablets, granules, and capsules. Dosage forms for parenteral administration include injection, suppositories, or percutaneous agents, which are administered intravenously, subcutaneously, intramuscularly, or intraperitoneally.

Physiologically active peptides such as MK or PTN are rapidly digested by protease in digestive tracts in general when they are administered orally. To stabilize MK or PTN in vivo, a hybrid MK or hybrid PTN should be prepared by binding it to water-soluble macromolecules (for example, polyethylene glycol (PEG) or polyvinylpyrrolidone (PVP)). Hybrid constructions of IL-6, TNF-α, etc. have been attempted, and the function has been enhanced by selecting the most suitable hybrid condition (Tsutsumi, Y. et al., Br. J. Cancer. 74: 1090–1095; Tsutsumi, Y. et al., Thoromb. Haemostasis, 77: 168–173, 1997; Tsutsumi, Y. et al., J. Control Release, 33: 447–451, 1995).

The MK family proteins that are effective ingredients of the pharmaceutical compositions of the invention vary depending on the dosage of the causative drug, severity of nephropathy or hepatopathy, age, sex, and weight of the patient when used to prevent or treat nephropathy or hepatopathy caused by drugs. The proteins of the invention can be administered once or several times at a dosage of 1 μg/kg to 100 mg/kg of body weight per day.

BRIEF DESCRIPTION OF THE DRAWINGS

FIGS. 11A–E shows the amino acid sequence of PTN proteins. FIG. 11A shows the sequence from human (SEQ ID NO. 1). FIG. 11B shows the sequence from mouse (SEQ ID NO. 2). FIG. 11C shows the sequence from rat (SEQ ID NO. 3). FIG. 11D shows the sequence from bovine (SEQ ID NO. 4). FIG. 11E shows the sequence from chicken (SEQ ID NO. 5).

FIGS. 12A–D shows the amino acid sequence of MK proteins. FIG. 12A shows the sequence from human (SEQ ID NO. 6). FIG. 12B shows the sequence from mouse (SEQ ID NO. 7). FIG. 12C shows the sequence from chicken (SEQ ID NO. 8). FIG. 12D shows the sequence from *Xenopus laevis* (SEQ ID NO. 9).

BEST MODE FOR IMPLEMENTING THE INVENTION

The present invention is illustrated in detail below with reference to examples, but is not to be construed as being limited thereto.

EXAMPLE 1

Effect of MK on Relieving Nephropathy in Vivo

Figure 1:
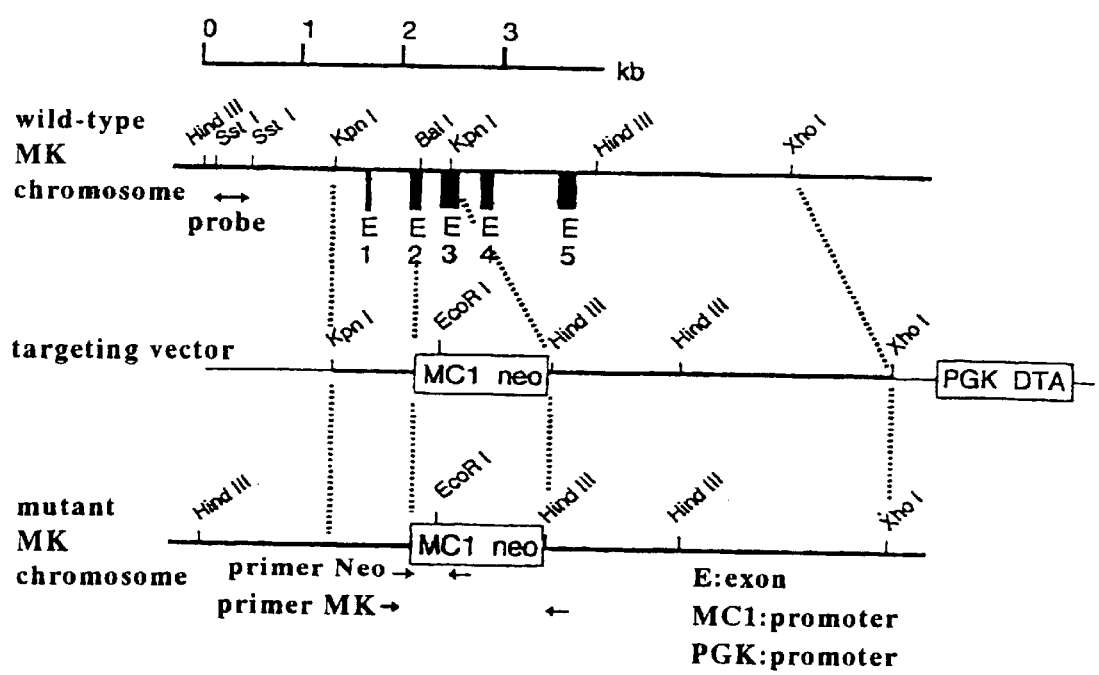
FIG. 1 shows the mutant chromosome of the knockout mouse in which parts of exons 2 and 3 of MK gene of 129/Sv mice was destroyed.
Figure 2:
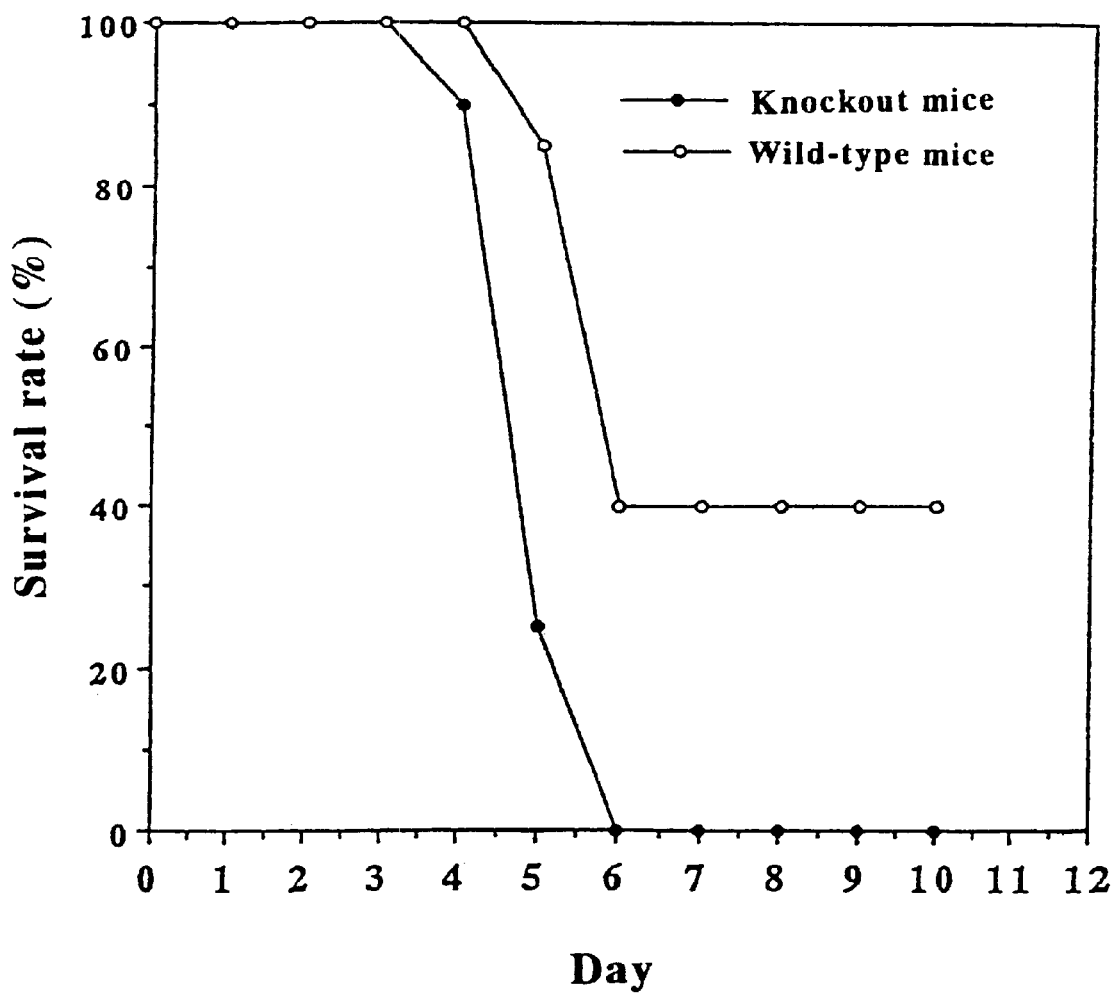
FIG. 2 shows the survival rate of 129/Sv MK knockout mice and that of wild mice after the administration of cisplatin.
Figure 3:
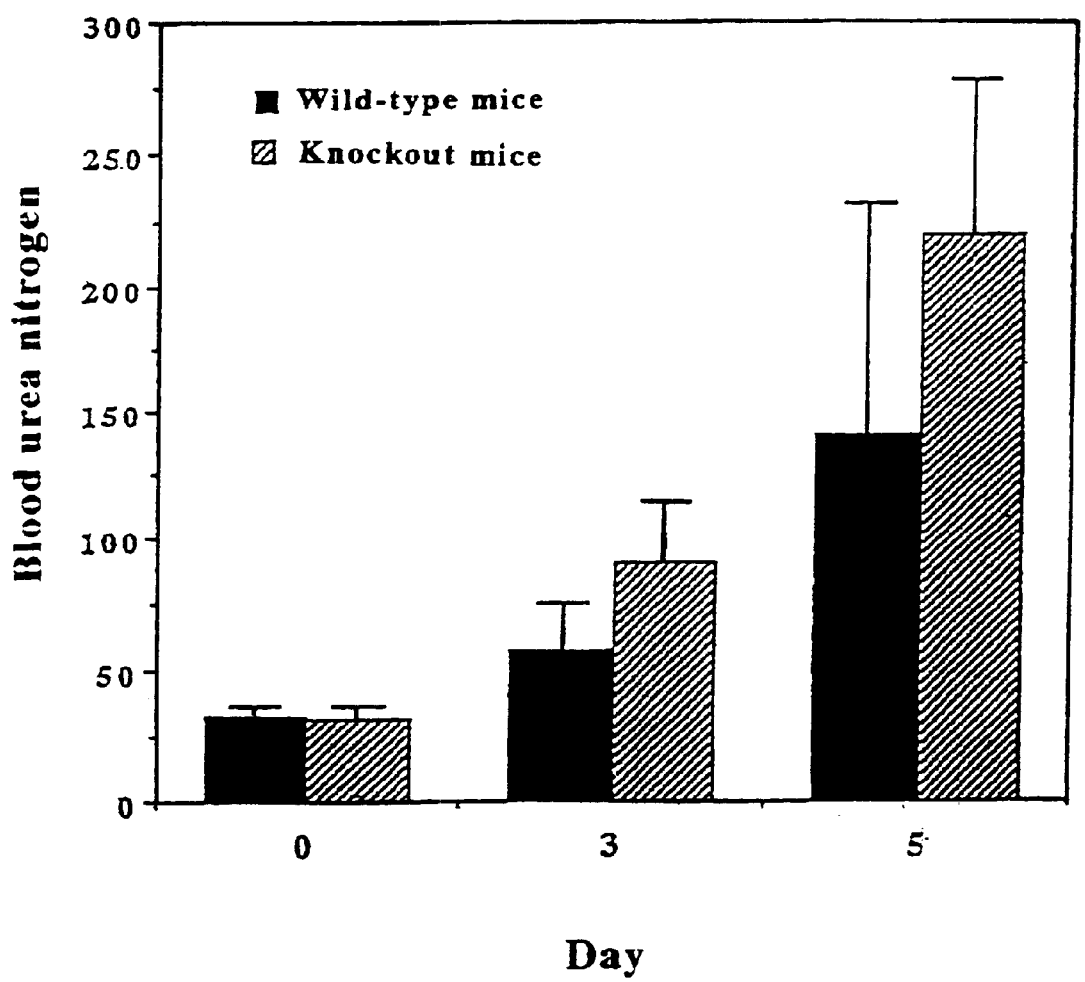
FIG. 3 shows blood urea nitrogen of 129/Sv MK knockout mice and that of wild mice on the day of administration and on the third and fifth days after the administration of cisplatin.

The 129/Sv knockout mice in which parts of exons 2 and 3 of MK genes were destroyed as illustrated in FIG. 1 were used (Biochemistry 7, Volume 68, pp 1239, 4-p-1244, 1996; Nakamura, E. et al. Genes to Cells 3, 811–822, 1998). FIG. 2 shows the survival rate of the 129/Sv MK gene-knocked out mice and that of wild mice after the intraperitoneal administration of 14 mg/kg cisplatin (product name, briplatin, Bristol Myers Squibb Company). FIG. 3 shows BUN levels 0, 3, and 5 days after the administration of the cisplatin. Cisplatin was selected because it is the fastest, most effective, and most common antitumor agent against solid tumors. Moreover, the side effect of cisplatin is nephropathy such as acute renal failure and MK is expressed only in kidneys in adult mice.

The Student t test revealed that the BUN levels of knockout. mice were significantly higher than that of wild mice, as indicated in FIG. 3.

Figure 4:
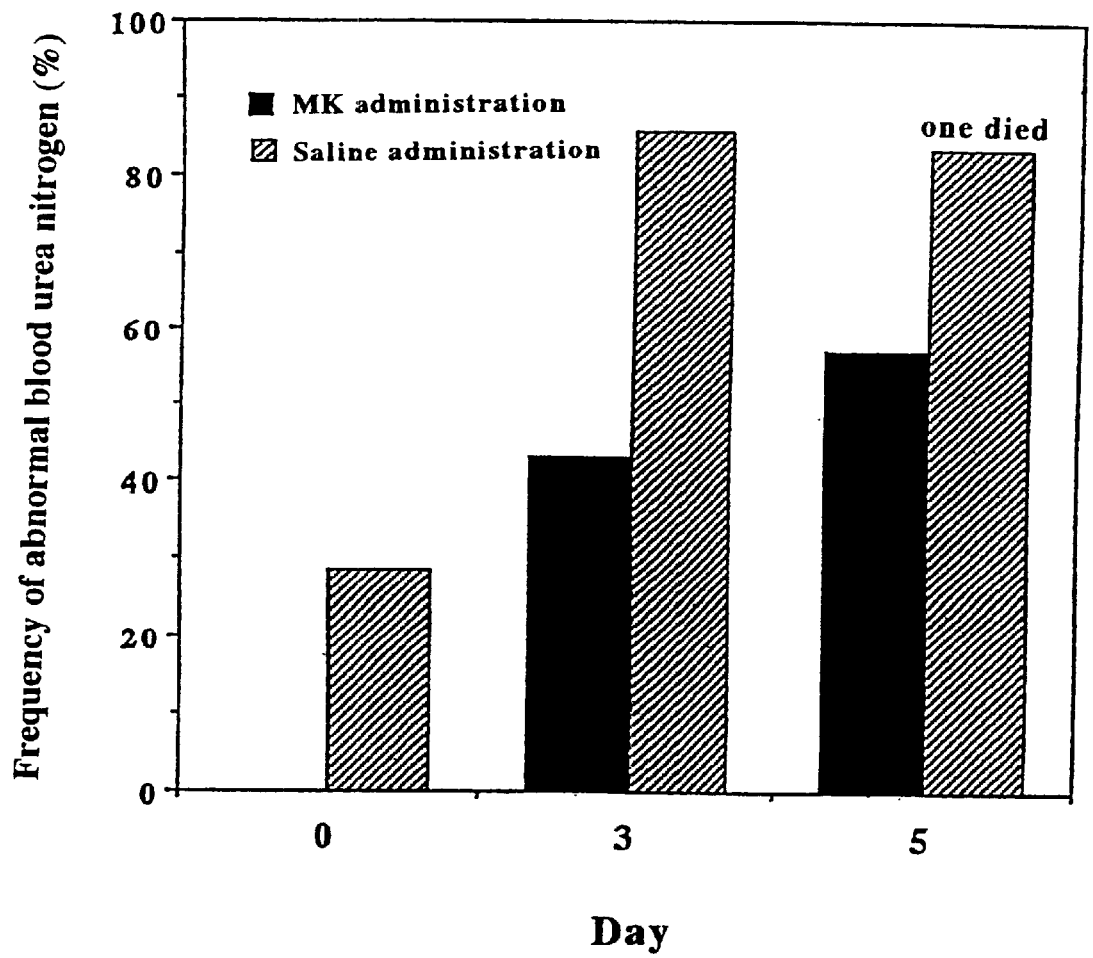
FIG. 4 shows the frequency of abnormal blood urea nitrogen of 129/Sv MK knockout mice on the day of administration and on the third and fifth days after 14 mg/kg cisplatin was administered and MK or physiological saline absorbed capsules for sustained release were intraperitoneally implanted.

FIG. 4 shows the frequency of abnormal blood urea nitrogen of mice at zero, three, and five days after the administration of 14 mg/kg of cisplatin; 207 mg of MK-containing sustained release capsules were intraperitoneally implanted in seven mice of the MK administration group, and 207 mg of physiological saline-containing sustained release capsules were intraperitoneally implanted in seven mice of the physiological saline administration group. The frequency of abnormality indicates the rate of occurrence of BUN abnormality when 50 BUN or more is the abnormal-level.

EXAMPLE 2

Effect of MK on Relieving Hepatopathy

Wild mice with acute hepatopathy caused by carbon tetrachloride were prepared. The effects of administering MK on relieving acute hepatopathy were then monitored. Five mice were employed for each treatment. Once carbon tetrachloride diluted to 10% with food oil "Medium Chain Triglyceride: Panasate 800" (NOF corporation) were administered to the mice, they were fasted. Physiological saline, 0.017 mg of MK or 1.7 mg of MK (JP-A No. Hei 9-95454), was administered intraperitoneally after 24 hours and again 8 hours after the first administration. Blood was collected after 16 hours, and serum GOT and GPT were measured (FIGS. 5 and 6).

Figure 5:
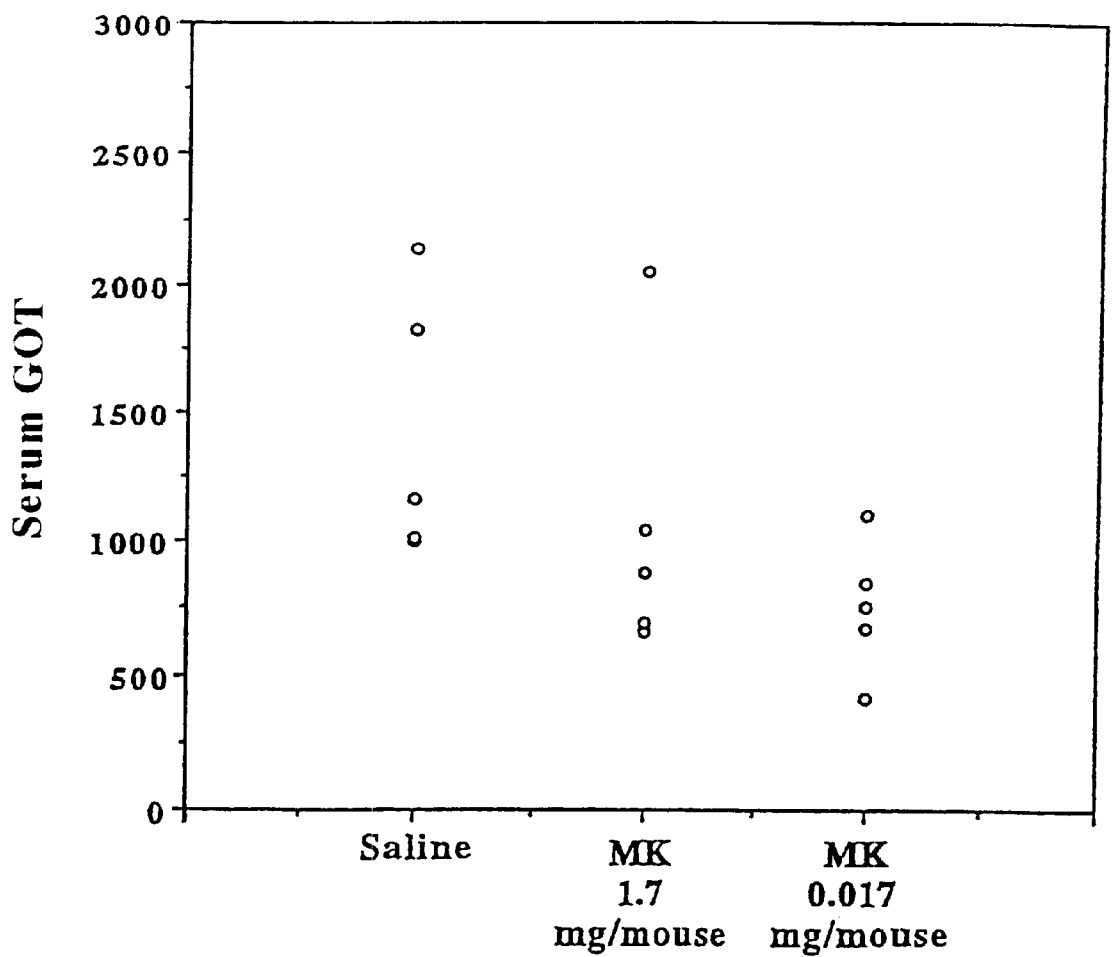
FIG. 5 shows the serum GOT of mice suffering from acute hepatopathy caused by carbon tetrachloride when various concentrations of MK or physiological saline were administered to the mice.
Figure 6:
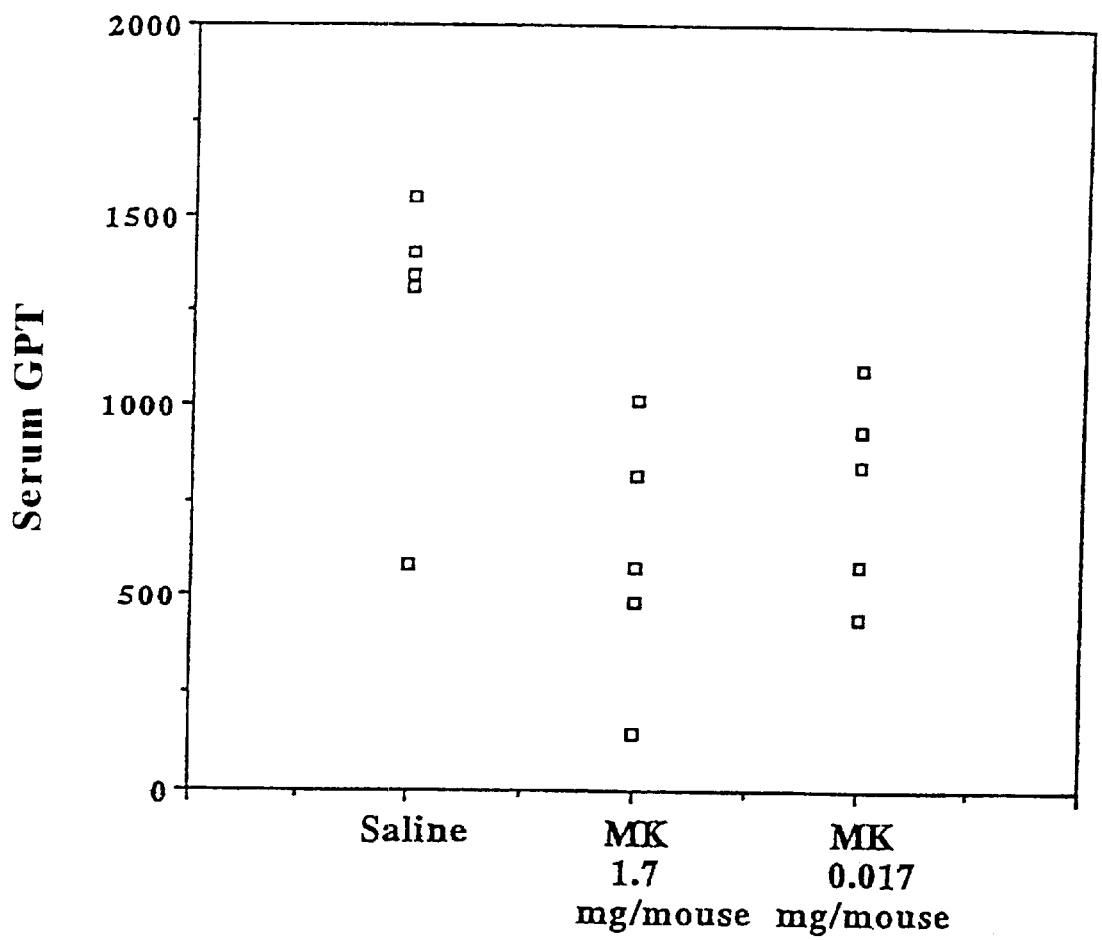
FIG. 6 shows the serum GTP of the same mice as in FIG. 5.

The Student t test revealed that the GOT of the physiological saline group did not significantly differ from that of the MK (1.7 mg) administration group as shown in FIGS. 5 and 6. In contrast, GPT between the groups differed significantly at the 5% risk level. It was thus determined that MK significantly relieved acute hepatopathy caused by carbon tetrachloride.

EXAMPLE 3

Effect of MK on Relieving Nephropathy

G401 cells derived from human infantile renal cancer (Wilms tumor) were used considering the side effects of antitumor agent cisplatin on kidneys.

G401 cells derived from human infantile renal cancer (Wilms tumor) were adjusted to $1 \times 10^5$ cells/ml or $3 \times 10^5$ cells/ml by 10% FBS/DME medium. $2 \times 10^4$ cells or $6 \times 10^4$ cells were inoculated per well of a 96-well plate (COSTAR: 3596) and incubated at 37° C. overnight under a 5% $CO_2$ atmosphere.

Subsequently, the cells were incubated in a 0.1% FBS/DME medium containing 2 $\mu$g/ml or 10 $\mu$g/ml of MK and in the same medium without MK as a control group for six hours. After the second incubation, the cells were incubated in a medium containing 10 $\mu$M of cisplatin (product name, briplatin, Bristol Myers Squibb Company) for 2 hours.

The cultured media were washed four times after the incubation, and the cell incubation was continued in a media containing 2 $\mu$g/ml or 10 $\mu$g/ml of MK the same as above.

Proliferation activity of the live cells was measured with Premix WST-1 Cell Proliferation Assay System (Takara) to evaluate the effect of MK on relieving nephropathy. Proliferation activity was assayed by intracellular division and proliferation of mitochondria reflected in absorbance (450 nm, control: 655 nm) in the same way as in an MTT assay.

Figure 7:
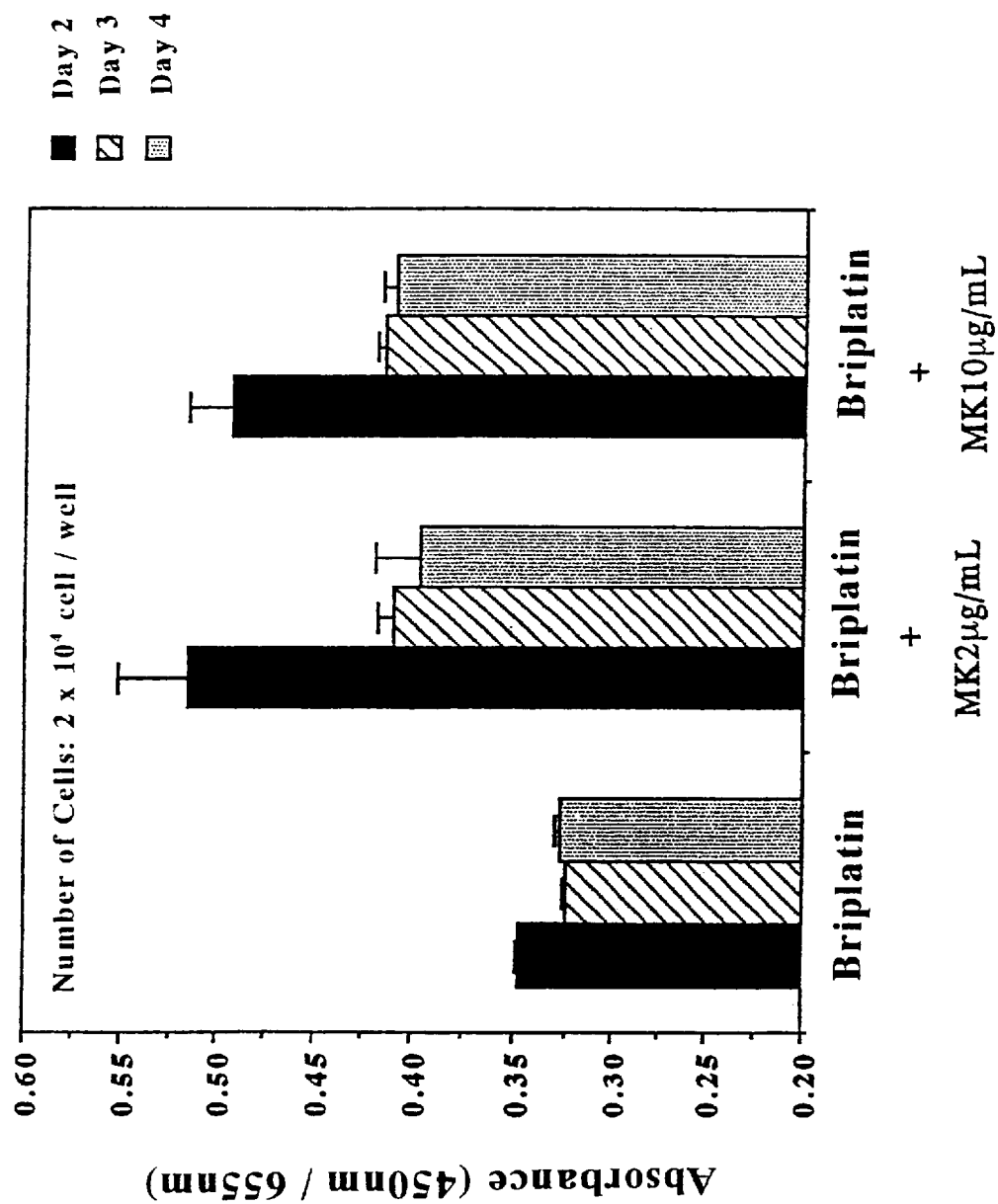
FIG. 7 shows the survival rate of G401 cells where $2 \times 10^4$ cells/well were cultured in the medium alone, the medium with 2 μg/ml of MK, or the medium with 10 μg/ml of MK, and treated with briplatin (cisplatin) during the culture.
Figure 8:
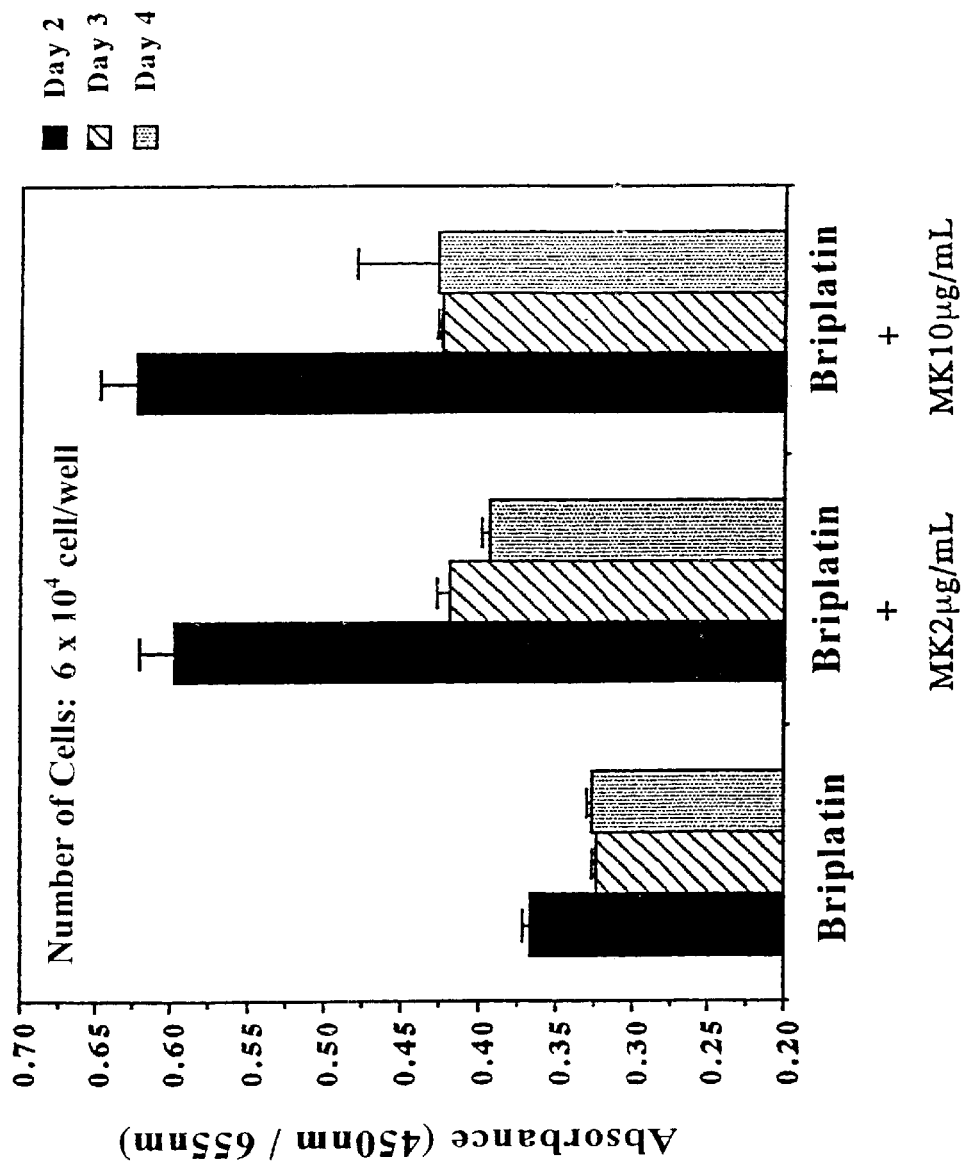
FIG. 8 shows the survival rate of G401 cells ($6 \times 10^4$ cells/well) after the same treatment as in FIG. 7.

Specifically, the cells were treated by cisplatin. Premix WST-1 reagent, up to $\frac{1}{10}$ of the medium, was then added to each well on the second, third, or fourth day after the cispaltin treatment, and the cells were incubated for 4 hours. The absorbance of each well was measured with a Plate Reader (BIO-RAD; Model 3550) (FIGS. 7 and 8). FIGS. 7 and 8 indicate that 2 to 10 $\mu$g/ml of MK dramatically decreased the number of G401 cell deaths due to cisplatin (antitumor agent) nearly two fold.

EXAMPLE 4

Effect of PTN on Relieving Drug-Induced Nephropathy

ICR mice (male, 8 to 10 week-old) were divided into two groups; one for physiological saline administration and the other for PTN administration (11 mice each). The dosages of PTN and physiological saline were 500 $\mu$g/kg for each group (Merenmies, J. and H. Rauvala: J. Biol. Chem. 265: 16721–16724, 1990). Briplatin (Bristol Myers Squibb Company) was used as cisplatin.

PTN or physiological saline was administered intraperitoneally to each mouse of the above two groups for three days continuously. On the fourth day, whole blood was collected from three mice of each group, and serum was prepared to serve as the serum sample before the administration of briplatin.

In the afternoon of the same day (the fourth day), 15 mg/kg of briplatin was intraperitoneally administered to each of the rest of mice. PTN or physiological saline was continuously administered to the rest of mice on each day until the seventh day. On the sixth and eighth days, whole blood was collected from the mice, and the serum was prepared to serve as the serum sample on the second and fourth days after the administration of briplatin.

Figure 9:
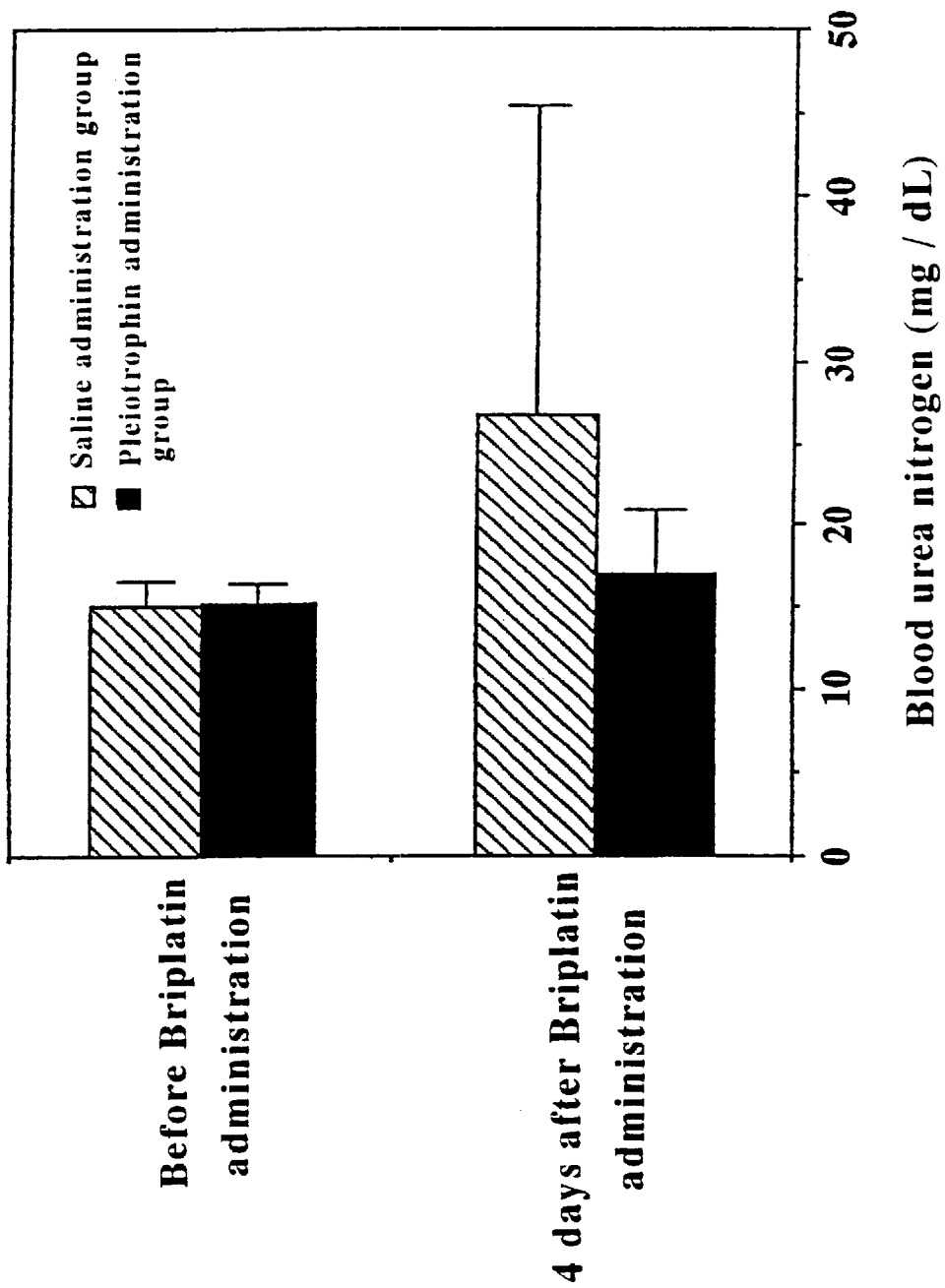
FIG. 9 shows BUN levels before and after the administration of briplatin (cisplatin) to mice during the administration of PTN or physiological saline.
Figure 10:
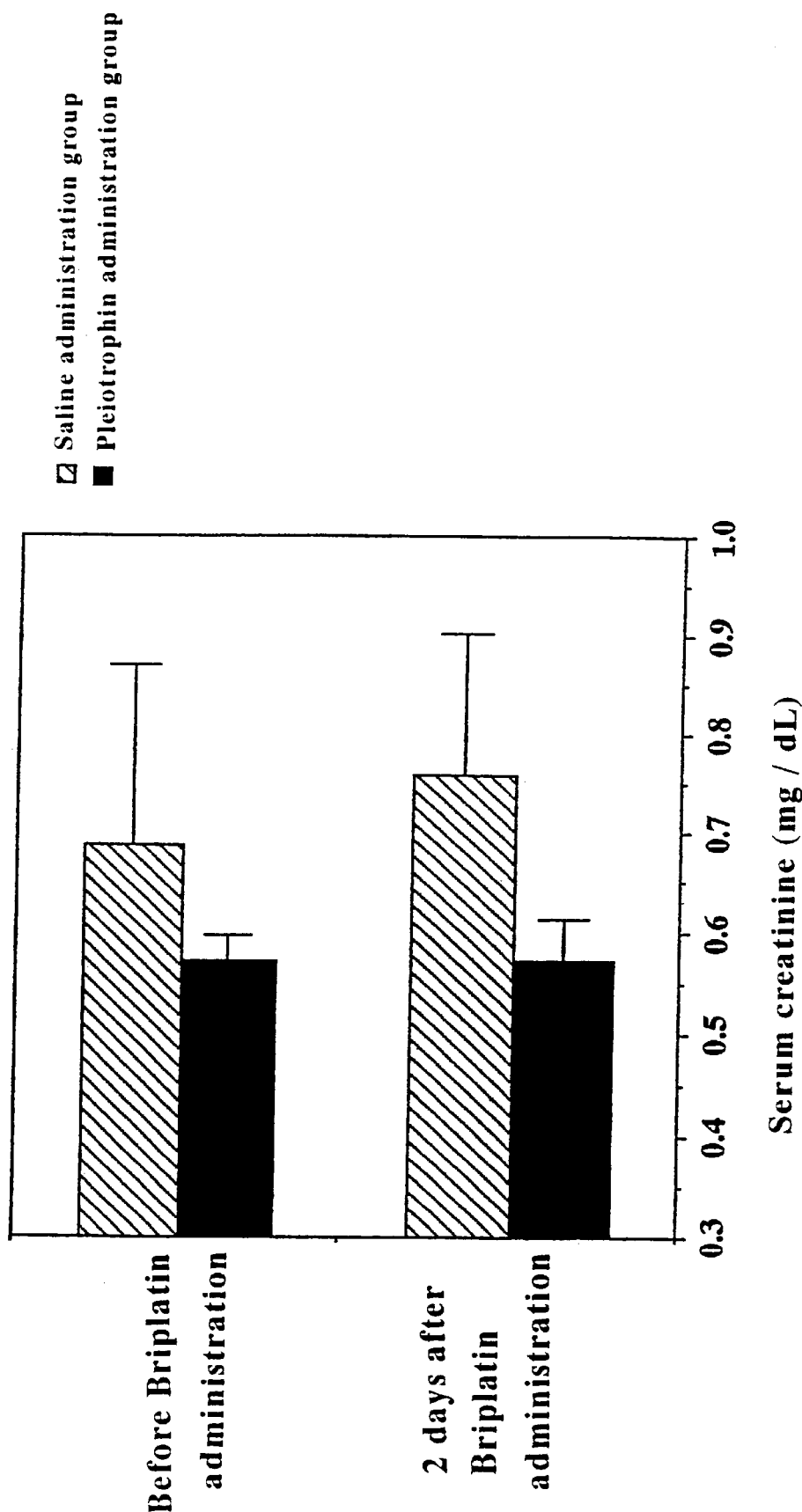
FIG. 10 shows the serum creatinine of the mice in FIG. 9.

Blood urea nitrogen (BUN), a representative marker of renal function, (FIG. 9) and serum creatinine (FIG. 10) of each sample were measured by Iatro-chrom UN (IATRON LABORATORIES, INC.) and Creatinine-test Wako (Wako Pure Chemical Industries, Ltd.), respectively. FIGS. 9 and 10 show that BUN and creatinine in the physiological saline administration group tended to be higher than that in the PTN administration group. These results indicate that both PTN and MK relieve drug-induced nephropathy.

Industrial Applicability

The present invention demonstrates that the MK family proteins effectively relieve drug-induced nephropathy and hepatopathy. Therefore, pharmaceutical composition of the invention, comprising MK family protein as an effective ingredient, is useful for relieving nephropathy and hepatopathy induced by drugs, especially antitumor agents.

What is claimed is:

1. A method for suppressing or treating nephropathy induced by cisplatin or an antitumor agent that acts by the same mechanism as cisplatin, wherein the method comprises administering midkine (MK) or pleiotropin (PTN) protein to a mammal.

2. The method according to claim 1, wherein said nephropathy is induced by cisplatin.

3. The method according to claim 1, wherein said nephropathy is acute renal failure.

4. The method according to claim 1, wherein said mechanism comprises cross-linking DNA.

* * * * *

SEQUENCE LISTING

<160> NUMBER OF SEQ ID NOS: 9

<210> SEQ ID NO 1
<211> LENGTH: 168
<212> TYPE: PRT
<213> ORGANISM: Homo sapiens

<400> SEQUENCE: 1

Met Gln Ala Gln Tyr Gln Gln Arg Arg Lys Phe Ala Ala Ala
1               5                   10                  15

Phe Leu Ala Phe Ile Phe Ile Leu Ala Ala Val Asp Thr Ala Glu Ala
                20                  25                  30

Gly Lys Lys Glu Lys Pro Glu Lys Lys Val Lys Lys Ser Asp Cys Gly
            35                  40                  45

Glu Trp Gln Trp Ser Val Cys Val Pro Thr Ser Gly Asp Cys Gly Leu
        50                  55                  60

Gly Thr Arg Glu Gly Thr Arg Thr Gly Ala Glu Cys Lys Gln Thr Met
65                  70                  75                  80

Lys Thr Gln Arg Cys Lys Ile Pro Cys Asn Trp Lys Lys Gln Phe Gly
                85                  90                  95

Ala Glu Cys Lys Tyr Gln Phe Gln Ala Trp Gly Glu Cys Asp Leu Asn
            100                 105                 110

Thr Ala Leu Lys Thr Arg Thr Gly Ser Leu Lys Arg Ala Leu His Asn
        115                 120                 125

Ala Glu Cys Gln Lys Thr Val Thr Ile Ser Lys Pro Cys Gly Lys Leu
    130                 135                 140

Thr Lys Pro Lys Pro Gln Ala Glu Ser Lys Lys Lys Lys Glu Gly
145                 150                 155                 160

Lys Lys Gln Glu Lys Met Leu Asp
                165

<210> SEQ ID NO 2
<211> LENGTH: 168
<212> TYPE: PRT
<213> ORGANISM: Mus sp.

<400> SEQUENCE: 2

Met Ser Ser Gln Gln Tyr Gln Gln Arg Arg Lys Phe Ala Ala Ala
1               5                   10                  15

Phe Leu Ala Leu Ile Phe Ile Leu Ala Ala Val Asp Thr Ala Glu Ala
                20                  25                  30

Gly Lys Lys Glu Lys Pro Glu Lys Lys Val Lys Lys Ser Asp Cys Gly
            35                  40                  45

Glu Trp Gln Trp Ser Val Cys Val Pro Thr Ser Gly Asp Cys Gly Leu
        50                  55                  60

Gly Thr Arg Glu Gly Thr Arg Thr Gly Ala Glu Cys Lys Gln Thr Met
65                  70                  75                  80

Lys Thr Gln Arg Cys Lys Ile Pro Cys Asn Trp Lys Lys Gln Phe Gly
                85                  90                  95

Ala Glu Cys Lys Tyr Gln Phe Gln Ala Trp Gly Glu Cys Asp Leu Asn
            100                 105                 110

```
Thr Ala Leu Lys Thr Arg Thr Gly Ser Leu Lys Arg Ala Leu His Asn
        115                 120                 125

Ala Glu Cys Gln Lys Thr Val Thr Ile Ser Lys Pro Cys Gly Lys Leu
    130                 135                 140

Thr Lys Pro Lys Pro Gln Ala Glu Ser Lys Lys Lys Lys Glu Gly
145                 150                 155                 160

Lys Lys Gln Glu Lys Met Leu Asp
                165

<210> SEQ ID NO 3
<211> LENGTH: 168
<212> TYPE: PRT
<213> ORGANISM: Rattus sp.

<400> SEQUENCE: 3

Met Ser Ser Gln Gln Tyr Gln Gln Arg Arg Lys Phe Ala Ala Ala
1               5                   10                  15

Phe Leu Ala Leu Ile Phe Ile Leu Ala Ala Val Asp Thr Ala Glu Ala
            20                  25                  30

Gly Lys Lys Glu Lys Pro Glu Lys Lys Val Lys Lys Ser Asp Cys Gly
            35                  40                  45

Glu Trp Gln Trp Ser Val Cys Val Pro Thr Ser Gly Asp Cys Gly Leu
    50                  55                  60

Gly Thr Arg Glu Gly Thr Arg Thr Gly Ala Glu Cys Lys Gln Thr Met
65                  70                  75                  80

Lys Thr Gln Arg Cys Lys Ile Pro Cys Asn Trp Lys Lys Gln Phe Gly
                85                  90                  95

Ala Glu Cys Lys Tyr Gln Phe Gln Ala Trp Gly Glu Cys Asp Leu Asn
            100                 105                 110

Thr Ala Leu Lys Thr Arg Thr Gly Ser Leu Lys Arg Ala Leu His Asn
        115                 120                 125

Ala Glu Cys Gln Lys Thr Val Thr Ile Ser Lys Pro Cys Gly Lys Leu
    130                 135                 140

Thr Lys Pro Lys Pro Gln Ala Glu Ser Lys Lys Lys Lys Glu Gly
145                 150                 155                 160

Lys Lys Gln Glu Lys Met Leu Asp
                165

<210> SEQ ID NO 4
<211> LENGTH: 168
<212> TYPE: PRT
<213> ORGANISM: Bos sp.

<400> SEQUENCE: 4

Met Gln Thr Pro Gln Tyr Leu Gln Gln Arg Arg Lys Phe Ala Ala Ala
1               5                   10                  15

Phe Leu Ala Phe Ile Phe Ile Leu Ala Ala Val Asp Thr Ala Glu Ala
            20                  25                  30

Gly Lys Lys Glu Lys Pro Glu Lys Lys Val Lys Lys Ser Asp Cys Gly
            35                  40                  45

Glu Trp Gln Trp Ser Val Cys Val Pro Thr Ser Gly Asp Cys Gly Leu
    50                  55                  60

Gly Thr Arg Glu Gly Thr Arg Thr Gly Ala Glu Cys Lys Gln Thr Met
65                  70                  75                  80

Lys Thr Gln Arg Cys Lys Ile Pro Cys Asn Trp Lys Lys Gln Phe Gly
                85                  90                  95
```

-continued

Ala Glu Cys Lys Tyr Gln Phe Gln Ala Trp Gly Glu Cys Asp Leu Asn
            100                 105                 110

Thr Ala Leu Lys Thr Arg Thr Gly Ser Leu Lys Arg Ala Leu His Asn
            115                 120                 125

Ala Glu Cys Gln Lys Thr Val Thr Ile Ser Lys Pro Cys Gly Lys Leu
            130                 135                 140

Thr Lys Ser Lys Pro Gln Ala Gly Ser Lys Lys Lys Lys Glu Gly
145                 150                 155                 160

Lys Lys Gln Glu Lys Met Leu Asp
                165

<210> SEQ ID NO 5
<211> LENGTH: 135
<212> TYPE: PRT
<213> ORGANISM: Gallus sp.

<400> SEQUENCE: 5

Gly Lys Lys Glu Lys Pro Glu Lys Lys Ala Lys Lys Ser Asp Cys Gly
1               5                   10                  15

Glu Trp Gln Trp Ser Val Cys Val Pro Thr Asn Gly Asp Cys Gly Leu
            20                  25                  30

Gly Thr Arg Glu Gly Thr Arg Thr Gly Ala Glu Cys Lys Gln Thr Thr
        35                  40                  45

Lys Thr Gln Lys Cys Lys Ile Pro Cys Asn Trp Lys Lys Gln Phe Gly
50                  55                  60

Ala Glu Cys Lys Tyr Gln Phe Gln Ala Trp Gly Glu Cys Asp Leu Asn
65                  70                  75                  80

Thr Ala Leu Lys Thr Arg Thr Gly Asn Leu Lys Arg Ala Leu His Asn
                85                  90                  95

Ala Glu Cys Gln Lys Thr Val Thr Ile Ser Lys Pro Cys Gly Lys Leu
            100                 105                 110

Thr Lys Pro Lys Pro Gln Glx Glu Lys Lys Lys Lys Glu Gly Lys
            115                 120                 125

Lys Gln Glu Lys Met Leu Asx
        130                 135

<210> SEQ ID NO 6
<211> LENGTH: 143
<212> TYPE: PRT
<213> ORGANISM: Homo sapiens

<400> SEQUENCE: 6

Met Gln His Arg Gly Phe Leu Leu Thr Leu Ala Leu Leu Ala
1               5                   10                  15

Leu Thr Ser Ala Val Ala Lys Lys Asp Lys Val Lys Lys Gly Gly
            20                  25                  30

Pro Gly Ser Glu Cys Ala Glu Trp Ala Trp Gly Pro Cys Thr Pro Ser
        35                  40                  45

Ser Lys Asp Cys Gly Val Gly Phe Arg Glu Gly Thr Cys Gly Ala Gln
            50                  55                  60

Thr Gln Arg Ile Arg Cys Arg Val Pro Cys Asn Trp Lys Lys Glu Phe
65                  70                  75                  80

Gly Ala Asp Cys Lys Tyr Lys Phe Glu Asn Trp Gly Ala Cys Asp Gly
                85                  90                  95

Gly Thr Gly Thr Lys Val Arg Gln Gly Thr Leu Lys Lys Ala Arg Tyr
            100                 105                 110

-continued

Asn Ala Gln Cys Gln Glu Thr Ile Arg Val Thr Lys Pro Cys Thr Pro
                115                 120                 125
Lys Thr Lys Ala Lys Ala Lys Ala Lys Lys Gly Lys Gly Lys Asp
130                 135                 140

<210> SEQ ID NO 7
<211> LENGTH: 140
<212> TYPE: PRT
<213> ORGANISM: Mus sp.

<400> SEQUENCE: 7

Met Gln His Arg Gly Phe Phe Leu Leu Ala Leu Leu Ala Leu Leu Val
1               5                   10                  15
Val Thr Ser Ala Val Ala Lys Lys Glu Lys Val Lys Lys Gly Ser
                20                  25                  30
Glu Cys Ser Glu Trp Thr Trp Gly Pro Cys Thr Pro Ser Ser Lys Asp
            35                  40                  45
Cys Gly Met Gly Phe Arg Glu Gly Thr Cys Gly Ala Gln Thr Gln Arg
        50                  55                  60
Val His Cys Lys Val Pro Cys Asn Trp Lys Lys Glu Phe Gly Ala Asp
65                  70                  75                  80
Cys Lys Tyr Lys Phe Glu Ser Trp Gly Ala Cys Asp Gly Ser Thr Gly
                85                  90                  95
Thr Lys Ala Arg Gln Gly Thr Leu Lys Lys Ala Arg Tyr Asn Ala Gln
                100                 105                 110
Cys Gln Glu Thr Ile Arg Val Thr Lys Pro Cys Thr Ser Lys Thr Lys
                115                 120                 125
Ser Lys Thr Lys Ala Lys Lys Gly Lys Gly Lys Asp
130                 135                 140

<210> SEQ ID NO 8
<211> LENGTH: 142
<212> TYPE: PRT
<213> ORGANISM: Gallus sp.

<400> SEQUENCE: 8

Met Gln Pro Arg Gly Leu Leu Leu Leu Ala Leu Leu Leu Leu Leu Ala
1               5                   10                  15
Ala Ala Ala Glu Ala Leu Ala Lys Lys Glu Lys Met Lys Lys Glu
                20                  25                  30
Gly Ser Glu Cys Gln Asp Trp His Trp Gly Pro Cys Ile Pro Asn Ser
            35                  40                  45
Lys Asp Cys Gly Leu Gly Tyr Arg Glu Gly Ser Cys Gly Asp Glu Ser
        50                  55                  60
Arg Lys Leu Lys Cys Lys Ile Pro Cys Asn Trp Lys Lys Lys Phe Gly
65                  70                  75                  80
Ala Asp Cys Lys Tyr Lys Phe Glu Ser Trp Gly Cys Ser Ala Lys
                85                  90                  95
Thr Gly Val Lys Thr Arg Ser Gly Ile Leu Lys Lys Ala Leu Tyr Asn
                100                 105                 110
Ala Glu Cys Glu Glu Val Val Tyr Val Ser Lys Pro Cys Thr Ala Lys
                115                 120                 125
Met Lys Ala Lys Ala Lys Lys Gly Lys Gly Lys Asp
130                 135                 140

<210> SEQ ID NO 9
<211> LENGTH: 142

```
<212> TYPE: PRT
<213> ORGANISM: Xenopus laevis

<400> SEQUENCE: 9

Met Glu Leu Arg Ala Phe Cys Val Ile Leu Leu Ile Thr Val Leu Ala
1               5                   10                  15

Val Ser Ser Gln Ala Ala Lys Asn Lys Lys Glu Lys Gly Lys Lys Gly
            20                  25                  30

Ala Ser Asp Cys Thr Glu Trp Thr Trp Gly Ser Cys Ile Phe Asn Ser
            35                  40                  45

Lys Asp Cys Gly Ala Gly Thr Arg Glu Gly Thr Cys Lys Glu Glu Thr
    50                  55                  60

Arg Lys Leu Lys Cys Lys Ile Leu Cys Asn Thr Lys Lys Ala Phe Gly
65                  70                  75                  80

Ala Asp Cys Lys Tyr Lys Phe Glu Asn Thr Gly Glu Cys Asn Ala Thr
                85                  90                  95

Thr Gly Asn Lys Val Arg Ser Gly Thr Leu Lys Lys Ala Leu Tyr Asn
                100                 105                 110

Ala Asp Cys Gln Gln Thr Val Glu Ala Thr Lys Pro Cys Ser Leu Lys
            115                 120                 125

Thr Lys Ser Lys Ser Lys Gly Lys Lys Gly Lys Gly Lys Glu
    130                 135                 140
```